United States Patent
Hinterding et al.

(10) Patent No.: US 7,928,093 B2
(45) Date of Patent: *Apr. 19, 2011

(54) AMINO-PROPANOL DERIVATIVES

(75) Inventors: Klaus Hinterding, Wittlingen (DE); Klemens Högenauer, Vienna (AT); Peter Nussbaumer, Vienna (AT)

(73) Assignee: Novartis AG, Basel (CH)

( * ) Notice: Subject to any disclaimer, the term of this patent is extended or adjusted under 35 U.S.C. 154(b) by 12 days.

This patent is subject to a terminal disclaimer.

(21) Appl. No.: 11/568,645

(22) PCT Filed: May 25, 2005

(86) PCT No.: PCT/EP2005/005685
§ 371 (c)(1), (2), (4) Date: Nov. 3, 2006

(87) PCT Pub. No.: WO2005/118523
PCT Pub. Date: Dec. 15, 2005

(65) Prior Publication Data
US 2007/0225260 A1    Sep. 27, 2007

(30) Foreign Application Priority Data
May 27, 2004 (GB) .................... 0411929.3

(51) Int. Cl.
*C07D 231/56* (2006.01)
*C09B 5/00* (2006.01)
(52) U.S. Cl. ............ 514/183; 548/416; 548/361.1
(58) Field of Classification Search ............ None
See application file for complete search history.

(56) References Cited

U.S. PATENT DOCUMENTS 5,948,820 A * 9/1999 Fujita et al. .......... 514/653
2006/0211656 A1 * 9/2006 Albert et al. .......... 514/80

FOREIGN PATENT DOCUMENTS

| EP | 0 778 263 | 6/1997 |
| WO | 02/076995 | 10/2002 |
| WO | WO 02/076995 | * 10/2002 |

OTHER PUBLICATIONS

Marins et al. J Lipid Res. Sterol side chain length and structure affect the clearance of chylomicron-like lipid emulsions in rats and mice. 39(2):302-312; 1998.*
Williams et al (Foye's Principles of Medicinal Chemistry, 5th Edition, pp. 50 and 59-61, 2002).*
Hogenauer et al (ChemMedChem 3:1027-1029, 2008).*

* cited by examiner

*Primary Examiner* — Brandon J Fetterolf
*Assistant Examiner* — Craig Ricci
(74) *Attorney, Agent, or Firm* — Hoxie & Associates, LLC

(57) ABSTRACT

A compound of formula (I) wherein $R_1$, $R_2$, $R_3$, $R_4$ and $R_5$ are as defined in the specification, processes for their production, their uses, in particular in transplantation, and pharmaceutical compositions containing them.

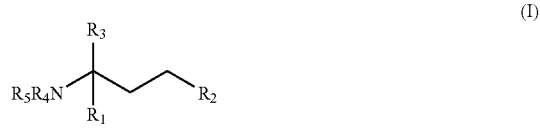

4 Claims, No Drawings

AMINO-PROPANOL DERIVATIVES

The present invention relates to amino-propanol derivatives, process for their production, their uses and pharmaceutical compositions containing them.

More particularly, the invention provides a compound of formula I

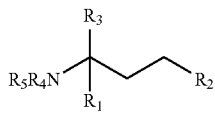

wherein $R_1$ is $C_{1-6}$alkyl optionally substituted by OH, $C_{1-2}$alkoxy or 1 to 6 fluorine atoms; $C_{2-6}$alkenyl; or $C_{2-6}$alkynyl;

$R_2$ is a radical of formula (a), (b) or (c)

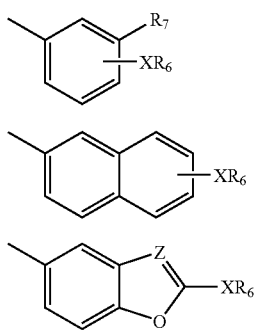

wherein $R_6$ is $C_{1-2}$alkyl optionally substituted by cycloalkyl, phenyl, heteroaryl, or a heterocyclic residue,
   wherein the $C_{1-12}$alkyl optionally is interrupted by one or more O or C=O; and
   wherein the phenyl, heteroaryl, cycloalkyl, and/or heterocyclic residue may be substituted by 1 to 5 substituents selected from hydroxy; halogen; $C_{1-4}$alkyl; $C_{1-4}$alkoxy; cyano; phenyl; and phenyl substituted by 1 to 5 substituents selected from hydroxy, halogen, $C_{1-4}$alkyl, $C_{1-4}$alkoxy, and cyano;

$R_7$ is H, phenyl, or heteroaryl, wherein the phenyl and/or heteroaryl independently may be substituted by 1 to 5 substituents selected from hydroxy; halogen; $C_{1-4}$alkyl; $C_{1-4}$alkyl substituted by 1 to 5 fluorine atoms; $C_{1-4}$alkoxy; $C_{1-4}$alkoxy substituted by 1 to 5 fluorine atoms; and cyano;

X is O, C=O, S or a bond;

Z is N or CH;

$R_3$ is a residue of formula (d) or (e)

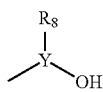

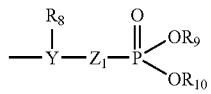

wherein Y is CH, or CF, $R_8$ is $C_{1-6}$alkyl; $C_{2-6}$alkenyl; $C_{2-6}$alkynyl; phenyl; $Z_1$ is a direct bond, $CH_2$, CHF, $CF_2$ or O, and each of $R_9$ and $R_{10}$, independently, is H or $C_{1-4}$alkyl optionally substituted by 1, 2 or 3 halogen atoms; and each of $R_4$ and $R_5$, independently, is H, $C_{1-4}$alkyl optionally substituted by 1, 2 or 3 halogen atoms, or acyl;

in free form or in salt form.

Alkyl or alkyl moiety may be straight or branched chain, e.g. methyl, ethyl, propyl, iso-propyl or butyl. Alkenyl may be e.g. vinyl. Cycloalkyl may be e.g. $C_{3-6}$cycloalkyl.

Acyl may be a residue W—CO wherein W is $C_{1-6}$alkyl, $C_{3-6}$cycloalkyl, phenyl or phenyl$C_{1-4}$alkyl.

Halogen may be F, Cl or Br, preferably F or Cl.

Heteroaryl may be a 5 to 8 membered aromatic ring comprising 1 to 4 heteroatoms selected from N, O and S, e.g. pyridyl, pyrimidinyl, pyrazinyl, furyl, oxazolyl, isoxazolyl, thienyl, thiazolyl, thiophenyl, isothiazolyl, pyrrolyl, imidazolyl, or pyrazolyl.

By heterocyclic residue is meant a 3 to 8, preferably 5 to 8, membered saturated or unsaturated heterocyclic ring comprising e.g. tetrahydrofuryl, tetrahydropyranyl, aziridinyl, piperidinyl, pyrrolidinyl, piperazinyl.

Compounds of formula I may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts. Compounds of formula I and their salts, in hydrate or solvate form are also part of the invention.

When the compounds of formula I have asymmetric centers in the molecule, various optical isomers are obtained. The present invention also encompasses enantiomers, racemates, diastereoisomers and mixtures thereof. For example, the central carbon atom bearing $R_1$, $R_3$ and $NR_4R_5$ may have the R or S configuration. Compounds having the following 3-dimensional configuration are generally preferred:

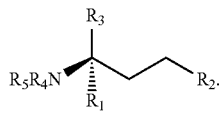

Moreover, when the compounds of formula I include geometric isomers, the present invention embraces cis-compounds, trans-compounds and mixtures thereof. Similar considerations apply in relation to starting materials exhibiting asymmetric carbon atoms or unsaturated bonds as mentioned above, e.g. compounds of formula II, or III as indicated below.

In the compounds of formula I, the following significances are preferred individually or in any sub-combination:
1. $R_1$ is $CH_3$ or $CH_2$—OH;
2. $R_3$ is a residue of formula —$CH(R_8)(OH)$ or of formula —$CH(R_8)(OPO(OR_9)(OR_{10}))$
3. each of $R_4$ and $R_5$ is hydrogen;
4. X is O or a bond;
5. $XR_6$ in formula (a) is para to the attachment to formula I;

6. in the naphthyl radical of formula (b), $XR_6$ is in position 5;
7. $R_7$ is hydrogen, phenyl or thiophenyl; and
8. $R_8$ is methyl, ethyl, ethynyl or phenyl;
9. $R_9$ is H;
10. $R_{10}$ is H.

The present invention also includes a process for the preparation of a compound of formula I which process comprises a) removing the protecting group present in a compound of formula II

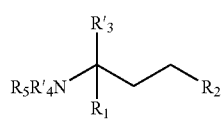

II wherein $R_1$, $R_2$ and $R_5$ are as defined above, $R'_3$ is $-Y(R_8)$(OH) wherein Y and $R_8$ are as defined above, and $R_{14}$ is an amino protecting group, b) removing the protecting group present in a compound of formula III

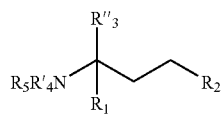

III wherein $R_1$, $R_2$, $R_{14}$ and $R_5$ are as defined above, $R'_3$ is a residue of formula (e')

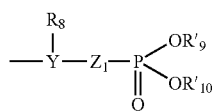

(e')

wherein Y, $Z_1$ and $R_8$ are as defined above, and each of $R'_9$ and $R'_{10}$, is a hydrolysable or hydrogenolysable group or $R'_9$ and $R'_{10}$ form together a divalent bridging residue optionally fused to a ring (e.g. benzene ring), and, where required, converting the compounds of formula I obtained in free form into the desired salt form, or vice versa.

Removal of protecting group may be carried out in accordance with methods known in the art. The removal of the amino protecting groups may conveniently be performed according to methods known in the art, e.g. by hydrolysis, e.g. in an acidic medium, for example using hydrochloric acid. Examples of protecting groups for amino groups are e.g. as disclosed in "Protective Groups in Organic Synthesis" T. W. Greene, J. Wiley & Sons NY, $2^{nd}$ ed., chapter 7, 1991, and references therein, e.g. benzyl, p-methoxybenzyl, methoxymethyl, tetrahydro-pyranyl, trialkylsilyl, acyl, tert.-butoxy-carbonyl, benzyloxycarbonyl, 9-fluorenyl methoxy carbonyl, trifluoroacetyl, and the like.

The present invention also includes a process for the preparation of a compound of formula II, wherein X is O or S, which process comprises alkylating a compound of formula IV

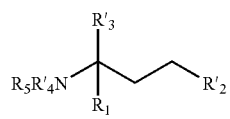

IV wherein $R_1$, $R_3'$, $R_4'$, $R_5$ are as defined above, and $R'_2$ is a radical of formula (a') or (b') or (c') or (d')

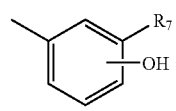

(a')

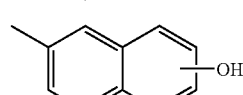

(b')

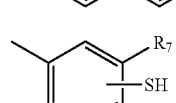

(c')

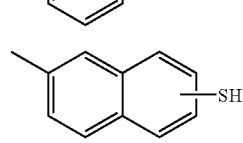

(d')

wherein $R_7$ is as defined above
to introduce the desired residue $R_6$.

Alkylation of the compounds of formula IV may be performed according to methods known in the art, e.g. by nucleophilic substitution, e.g. by reaction with an alkylating agent $R_6-X_3$ wherein $X_3$ is mesylate, tosylate, triflate, nosylate or an halogen, e.g. chloride, bromide or iodide. The alkylation may also be carried out by following the Mitsunobu protocol (e.g. as disclosed in Hughes, Organic Preparations and Procedures International 28, 127-64, 1996 or D. L. Hughes, Org. React. 42, 335, 1992), in solution or on solid phase support synthesis, e.g. by attaching the compound of formula IV to a resin. Alternatively, either triphenyl-phosphine or e.g. diethyl azocarboxylate bound to a resin, e.g. polystyrene, can be used.

Insofar as the production of the starting materials is not particularly described, the compounds are known or may be prepared analogously to methods known in the art or as disclosed in the Examples hereinafter. The following Examples are illustrative of the invention. Melting points are uncorrected.

RT=room temperature
DMF=N,N-dimethylformamide
AcOEt=ethyl acetate
THF=tetrahydrofuran
RP-HPLC=reversed phase high performance liquid chromatography
TFA=trifluoroacetic acid Scheme 1: Synthesis Overview.
Methods A, B, G and H are known in the art, and may be performed e.g. as disclosed in K. Hinterding et al, Synthesis 2003, 1667.
M may be any metal or metal salt used in addition reactions to aldehydes known in the art, e.g. MgCl, MgBr, MgI, Li, Zn, Cu.
PG means protecting group.
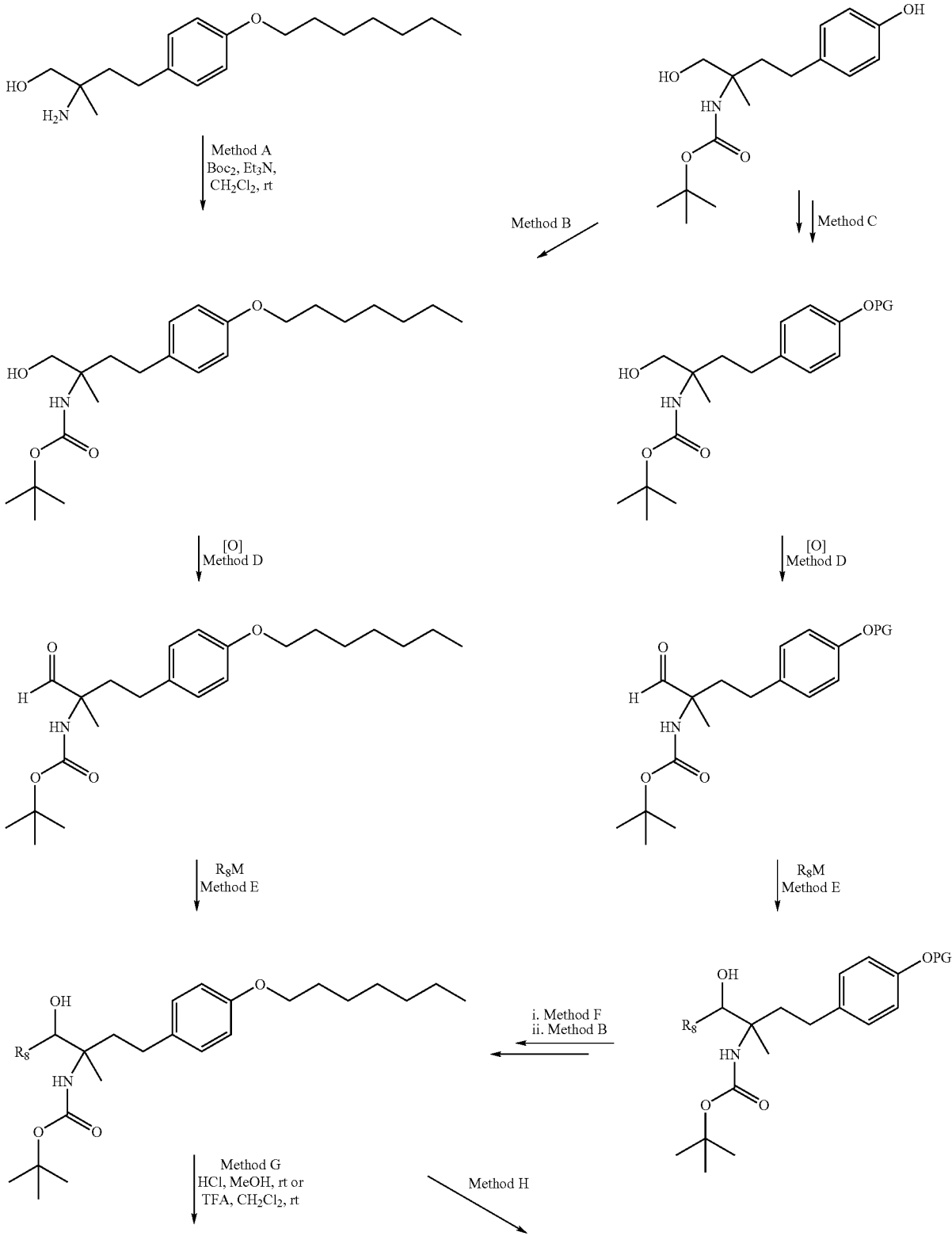

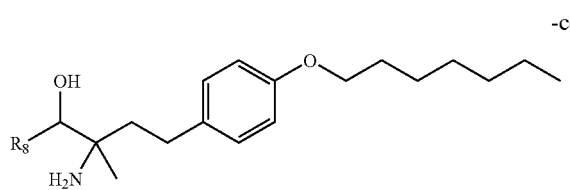
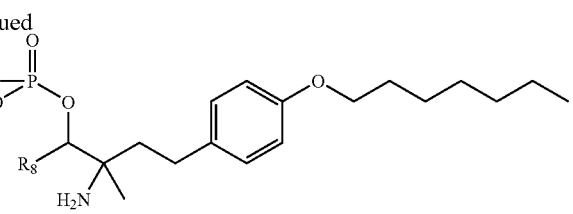

Preparation of [(R)-1-Formyl-3-(4-heptyloxy-phenyl)-1-methyl-propyl]-carbamic acid tert-butyl ester (Method D)

Preparation of {(R)-3-[4-(tert-Butyl-dimethyl-silanyloxy)-phenyl]-1-hydroxymethyl-1-methyl-propyl}-carbamic acid tert-butyl ester (Method C)

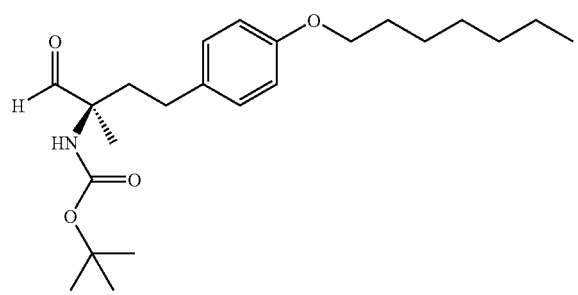

To a stirred solution of [(R)-1-hydroxymethyl-3-(4-heptyloxy-phenyl)-1-methyl-propyl]-carbamic acid tert-butyl ester (1.98 g, 5.03 mMol) in CH$_2$Cl$_2$ (20 ml) is added N-morpholine-N-oxide (884 mg, 7.54 mMol) and tetra-n-propylammonium perruthenate (177 mg, 0.50 mMol). The mixture is stirred at RT for 1 hour. The mixture is then filtered over a short pad of SiO$_2$ eluting with diethyl ether. The filtrate is concentrated under reduced pressure to give the title compound. The crude product is sufficiently pure to be used in the next stage without further purification.

$^1$H-NMR (CDCl$_3$): 9.33 (s, 1H), 7.06-7.01 (m, 2H), 6.82-6.76 (m, 2H), 5.18 (br s, 1H), 3.92 (t, 2H), 2.60-2.49 (m, 1H), 2.44-2.19 (m, 2H), 2.01-1.93 (m, 1H), 1.80-1.71 (m, 2H), 1.55 (s, 3H), 1.48-1.25 (m, 17H), 0.89 (t, J=7 Hz, 3H). MS (ESI+): m/z=414.2 [M+Na]$^+$.

Preparation of {(R)-3-[4-(tert-Butyl-dimethyl-silanyloxy)-phenyl]-1-formyl-1-methyl-propyl}-carbamic acid tert-butyl ester The title compound is prepared as described above (Method D).
MS (ESI+): m/z=430.2 [M+Na]$^+$, 837.5 [2M+Na]$^+$

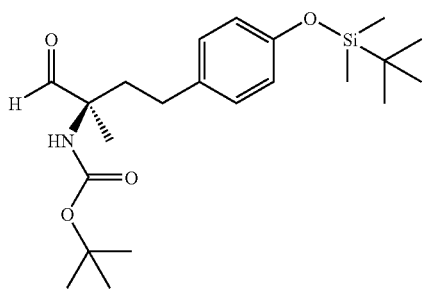

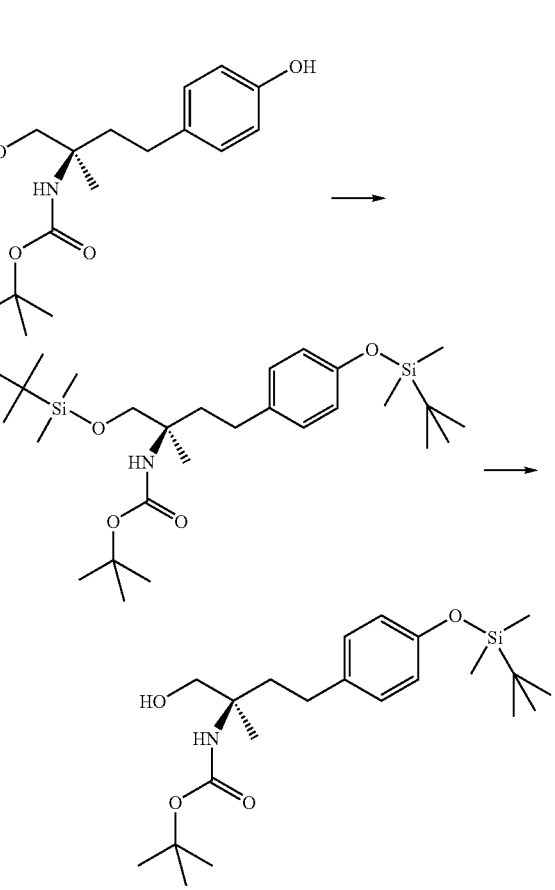

To a stirred solution of [(R)-1-Hydroxymethyl-3-(4-hydroxy-phenyl)-1-methyl-propyl]-carbamic acid tert-butyl ester (1.0 g, 3.39 mMol) in DMF (2 ml) is added imidazole (1.15 g, 16.9 mMol) and tert-Butyldimethylsilyl chloride (1.28 g, 8.49 mMol). The reaction is stirred at RT for 6 hours. The reaction mixture is then poured onto a biphasic mixture of AcOEt and NaHCO$_3$ (saturated aqueous solution). The aqueous phase is extracted twice with AcOEt. The combined organic layers are dried (Na$_2$SO$_4$) and concentrated under reduced pressure. Column chromatography eluting with 3% AcOEt in heptane gives {(R)-1-(tert-Butyl-dimethyl-silanyloxymethyl)-3-[4-(tert-butyl-dimethyl-silanyloxy)-phenyl]-1-methyl-propyl}-carbamic acid tert-butyl ester as a colourless oil.
MS (ESI+): m/z=546.3 [M+Na]$^+$, 1069.5 [2M+Na]$^+$.

To a stirred solution of {(R)-1-(tert-Butyl-dimethyl-silanyloxymethyl)-3-[4-(tert-butyl-dimethyl-silanyloxy)-phenyl]-

1-methyl-propyl}-carbamic acid tert-butyl ester (8.84 g, 16.8 mMol) in acetonitrile (150 ml) is added H$_2$O (1.52 ml, 84.3 mMol) and Sc(OTf)$_3$ (83 mg, 0.2 mMol). The reaction is stirred at RT for 3 hours. The reaction mixture is then poured onto a biphasic mixture of AcOEt and NaHCO$_3$ (saturated aqueous solution). The aqueous phase is extracted with AcOEt (3 times). The combined organic layers are dried (Na$_2$SO$_4$) and concentrated under reduced pressure. Column chromatography eluting with 0%→40% AcOEt in heptane gives {(R)-3-[4-(tert-Butyl-dimethyl-silanyloxy)-phenyl]-1-hydroxymethyl-1-methyl-propyl}-carbamic acid tert-butyl ester as a colourless oil.

MS (ESI+): m/z=473.2 [M+Na$^+$ CH$_3$CN]$^+$, 841.3 [2M+Na]$^+$.

Preparation of {(1R,2R)-1-[2-(4-Heptyloxy-phenyl)-ethyl]-2-hydroxy-1-methyl-propyl}-carbamic acid tert-butyl ester and {(1R,2S)-1-[2-(4-Heptyloxy-phenyl)-ethyl]-2-hydroxy-1-methyl-propyl}-carbamic acid tert-butyl ester (Method E)

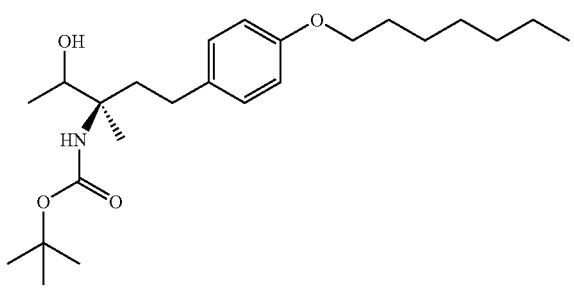

A stirred solution of [(R)-1-Formyl-3-(4-heptyloxy-phenyl)-1-methyl-propyl]-carbamic acid tert-butyl ester (380 mg, 0.97 mMol) in diethyl ether (3 ml) is cooled to 0° C. MeMgBr (1.62 ml, 3.0 M in Et$_2$O, 4.9 mMol) is added and the reaction is stirred at 0° C. for 1.25 hours. The reaction mixture is then poured onto a biphasic mixture of AcOEt and NH$_4$Cl (saturated aqueous solution). The aqueous phase is extracted with AcOEt (3 times). The combined organic layers are dried (Na$_2$SO$_4$) and concentrated under reduced pressure. Column chromatography eluting with 20% AcOEt in heptane gives a mixture of the title compounds (d.r.=3:1). The diastereomers are separated by RP-HPLC on a ZORBAX Extend C-18 column eluting with 5%→95% CH$_3$CN in H$_2$O (+0.1% TFA).

(1R,2R): $^1$H-NMR (CDCl$_3$): 7.10-7.02 (m, 2H), 6.82-6.77 (m, 2H), 4.58 (br s, 1H), 3.92 (t, 2H), 3.86 (d, J=7 Hz, 1H), 3.83 (d, J=7 Hz, 1H), 2.60-2.48 (m, 2H), 2.10-2.00 (m, 1H), 1.79-1.71 (m, 2H), 1.70-1.61 (m, 1H), 1.48-1.25 (m, 20H), 1.25 (d, J=6 Hz, 3H), 0.89 (t, J=7 Hz, 3H). [α]$_{25}^D$=−5.4 (c=0.65, CHCl$_3$).

(1R,2S): $^1$H-NMR (CDCl$_3$): 7.11-7.06 (m, 2H), 6.83-6.78 (m, 2H), 4.56 (br s, 1H), 3.92 (t, 2H), 3.82 (d, J=7 Hz, 1H), 3.78 (d, J=7 Hz, 1H), 2.63 (dt, J=5 Hz, 12 Hz, 1H), 2.48 (dt, J=5 Hz, 12 Hz, 1H), 2.15 (dt, J=5 Hz, 12 Hz, 1H), 1.95 (dt, J=5 Hz, 12 Hz, 1H), 1.78-1.70 (m, 2H), 1.70-1.25 (m, 17H), 1.19 (d, J=7H, 3H), 1.15 (s, 3H), 0.89 (t, J=7 Hz, 3H). [α]$_{25}^D$=−8.0 (c=1.0, CHCl$_3$).

Preparation of [(1S,2S)-1-[2-(4-Heptyloxy-phenyl)-ethyl]-2-hydroxy-1-methyl-propyl]-carbamic acid tert-butyl ester and ((1S,2R)-1-[2-(4-Heptyloxy-phenyl)-ethyl]-2-hydroxy-1-methyl-propyl)-carbamic acid tert-butyl ester The title compounds are prepared as described above (Method E).

(1S,2S): $^1$H-NMR (CDCl$_3$): 7.10-7.02 (m, 2H), 6.82-6.77 (m, 2H), 4.58 (br s, 1H), 3.92 (t, 2H), 3.86 (d, J=7 Hz, 1H), 3.83 (d, J=7 Hz, 1H), 2.60-2.48 (m, 2H), 2.10-2.00 (m, 1H), 1.79-1.71 (m, 2H), 1.70-1.61 (m, 1H), 1.48-1.25 (m, 20H), 1.25 (d, J=6 Hz, 3H), 0.89 (t, J=7 Hz, 3H). [α]$_{25}^D$=+5.3 (c=0.65, CHCl$_3$).

(1S,2R): $^1$H-NMR (CDCl$_3$): 7.11-7.06 (m, 2H), 6.83-6.78 (m, 2H), 4.56 (br s, 1H), 3.92 (t, 2H), 3.82 (d, J=7 Hz, 1H), 3.78 (d, J=7 Hz, 1H), 2.63 (dt, J=5 Hz, 12 Hz, 1H), 2.48 (dt, J=5 Hz, 12 Hz, 1H), 2.15 (dt, J=5 Hz, 12 Hz, 1H), 1.95 (dt, J=5 Hz, 12 Hz, 1H), 1.78-1.70 (m, 2H), 1.70-1.25 (m, 17H), 1.19 (d, J=7H, 3H), 1.15 (s, 3H), 0.89 (t, J=7 Hz, 3H). [α]$_{25}^D$=+9.5 (c=1.2, CHCl$_3$).

Preparation of {(1R,2R)-1-{2-[4-(tert-Butyl-dimethyl-silanyloxy)-phenyl]-ethyl}-2-hydroxy-1-methyl-propyl)-carbamic acid tert-butyl ester and ((1S,2R)-1-{2-[4-(tert-Butyl-dimethyl-silanyloxy)-phenyl]-ethyl}-2-hydroxy-1-methyl-propyl)-carbamic acid tert-butyl ester The title compounds are prepared as described above (Method E).

MS (ESI+): m/z=869.4 [2M+Na]$^+$.

Preparation of {(1R,2R)-2-Hydroxy-1-[2-(4-hydroxy-phenyl)-ethyl]-1-methyl-propyl}-carbamic acid tert-butyl ester (Method F)

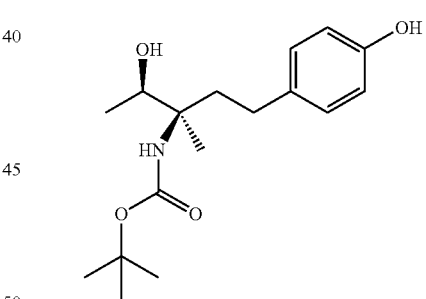

To a stirred solution of ((1R,2R)-1-{2-[4-(tert-Butyl-dimethyl-silanyloxy)-phenyl]-ethyl}-2-hydroxy-1-methyl-propyl)-carbamic acid tert-butyl ester (19 mg, 0.045 mMol) in acetonitril (2 ml) is added HF (0.2 ml, 40% solution), and the reaction is stirred at RT for 3.5 hours. The reaction mixture is then poured onto a biphasic mixture of AcOEt and NaHCO$_3$ (saturated aqueous solution). The aqueous phase is extracted with AcOEt (3 times). The combined organic layers are dried (Na$_2$SO$_4$) and concentrated under reduced pressure. Column chromatography eluting with 30% AcOEt in heptane gives the title compound.

$^1$H-NMR (CDCl$_3$): 7.03 (d, J=9 Hz, 2H), 6.72 (d, J=9 Hz, 2H), 4.58 (br s, 1H), 3.80 (q, J=6 Hz, 1H), 2.62 (dt, J=5 Hz, 13 Hz, 1H), 2.46 (dt, J=5 Hz, 13 Hz, 1H), 2.19 (dt, J=5 Hz, 13 Hz, 1H), 1.95 (dt, J=5 Hz, 13 Hz, 1H), 1.45 (s, 9H), 1.20 (d, J=7 Hz, 3H), 1.15 (s, 3H).

EXAMPLE 1

(2R,3R)-3-Amino-5-(4-heptyloxy-phenyl)-3-methyl-pentan-2-ol

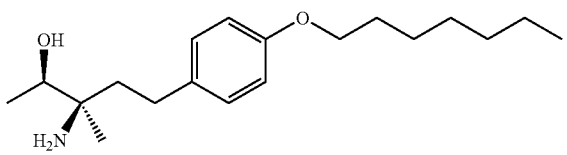

{(1R,2R)-1-[2-(4-Heptyloxy-phenyl)-ethyl]-2-hydroxy-1-methyl-propyl}-carbamic acid tert-butyl ester (30 mg, 0.074 mMol) is dissolved in a saturated solution of HCl in methanol. The solution is stirred at RT for 2 hours. After removing the solvent under reduced pressure, the compound is purified by trituration with Et$_2$O and is obtained as its hydrochloride salt.

$^1$H-NMR (CDCl$_3$): 8.12 (br s, 3H), 7.09 (d, J=9 Hz, 2H), 6.72 (d, J=9 Hz, 2H), 4.60 (br s, 1H), 4.07-4.00 (m, 1H), 3.85 (t, J=7 Hz, 2H), 2.79-2.70 (m, 2H), 1.97-1.88 (m, 2H), 1.77-1.61 (m, 2H), 1.47-1.23 (m, 11H), 1.20 (d, J=6 Hz, 3H), 0.85 (t, J=7 Hz, 3H). MS (ESI+): m/z=308.2 [M+H]$^+$.

EXAMPLE 2

(2S,3R)-3-Amino-5-(4-heptyloxy-phenyl)-3-methyl-pentan-2-ol

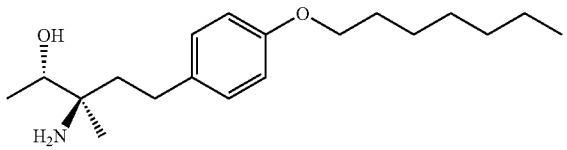

The title compound is prepared as described in Example 1 using appropriate starting materials. The compound was lyophilized from dioxane to give a white, amorphous powder.

$^1$H-NMR (d6-DMSO): 7.79 (br s, 3H), 7.09 (d, J=9 Hz, 2H), 6.82 (d, J=9 Hz, 2H), 5.39 (d, J=5 Hz, 1H), 3.90 (t, J=7 Hz, 2H), 3.72-3.63 (m, 1H), 2.65-2.45 (m, 2H), 1.81 (dt, J=4 Hz, 13 Hz, 1H), 1.70-1.58 (m, 3H), 1.42-1.22 (m, 8H), 1.20 (s, 3H), 1.11 (d, J=7 Hz, 3H), 0.85 (t, J=7 Hz, 3H). MS (ESI+): m/z=308.2 [M+H]$^+$.

EXAMPLE 3

(2S,3S)-3-Amino-5-(4-heptyloxy-phenyl)-3-methyl-pentan-2-ol

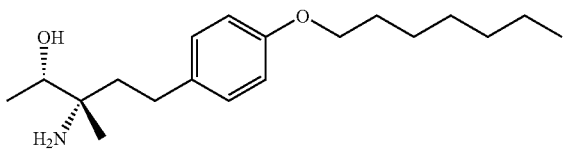

The title compound is prepared as described in Example 1 using appropriate starting materials. The compound is purified by digeration with Et$_2$O and is obtained as its hydrochloride salt.

$^1$H-NMR (CDCl$_3$): 8.12 (br s, 3H), 7.09 (d, J=9 Hz, 2H), 6.72 (d, J=9 Hz, 2H), 4.60 (br s, 1H), 4.07-4.00 (m, 1H), 3.85 (t, J=7 Hz, 2H), 2.79-2.70 (m, 2H), 1.97-1.88 (m, 2H), 1.77-1.61 (m, 2H), 1.47-1.23 (m, 11H), 1.20 (d, J=6 Hz, 3H), 0.85 (t, J=7 Hz, 3H). MS (ESI+): m/z=308.2 [M+H]$^+$.

EXAMPLE 4

(2R,3S)-3-Amino-5-(4-heptyloxy-phenyl)-3-methyl-pentan-2-ol

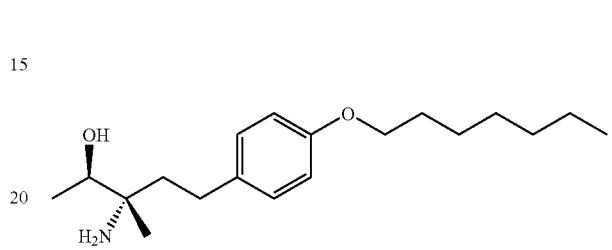

The title compound is prepared as described in Example 1 using appropriate starting materials. The compound was lyophilized from dioxane to give a white, amorphous powder.

$^1$H-NMR (d6-DMSO): 7.79 (br s, 3H), 7.09 (d, J=9 Hz, 2H), 6.82 (d, J=9 Hz, 2H), 5.39 (d, J=5 Hz, 1H), 3.90 (t, J=7 Hz, 2H), 3.72-3.63 (m, 1H), 2.65-2.45 (m, 2H), 1.81 (dt, J=4 Hz, 13 Hz, 1H), 1.70-1.58 (m, 3H), 1.42-1.22 (m, 8H), 1.20 (s, 3H), 1.11 (d, J=7 Hz, 3H), 0.85 (t, J=7 Hz, 3H). MS (ESI+): m/z=308.2 [M+H]$^+$.

EXAMPLE 5

(3R,4R)-4-Amino-6-(4-heptyloxy-phenyl)-4-methyl-hexan-3-ol

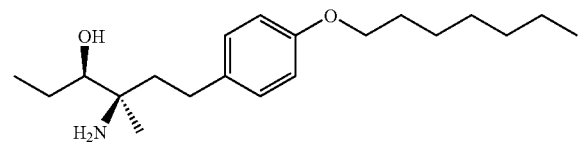

To a stirred solution of {(1R,2R)-1-[2-(4-Heptyloxy-phenyl)-ethyl]-2-hydroxy-1-methyl-butyl}-carbamic acid tert-butyl ester (25 mg, 0.06 mMol) in CH$_2$Cl$_2$ (3 ml) is added TFA (0.3 ml). The solution is stirred at RT for 2 hours. After removing the solvent under reduced pressure, the residue is lyophilized from dioxane to give the title compound as its trifluoroacetate salt as a white, amorphous powder.

$^1$H-NMR (d6-DMSO): 7.69 (br s, 3H), 7.08 (d, J=9 Hz, 2H), 6.83 (d, J=9 Hz, 2H), 5.41 (d, J=6 Hz, 1H), 3.90 (t, J=7 Hz, 2H), 3.35-3.22 (m, 1H), 2.60-2.45 (m, 2H), 1.81 (dt, J=4 Hz, 13 Hz, 1H), 1.70-1.44 (m, 5H), 1.40-1.25 (m, 11H), 0.92 (t, J=7 Hz, 3H), 0.85 (t, J=7 Hz, 3H). MS (ESI+): m/z=322.2 [M+H]$^+$.

EXAMPLE 6

(3S,4R)-4-Amino-6-(4-heptyloxy-phenyl)-4-methyl-hexan-3-ol

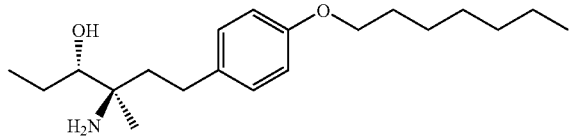

The title compound is prepared as described in Example 5 using appropriate starting materials. The compound was lyophilized from dioxane to give a white, amorphous powder.

$^1$H-NMR (d6-DMSO): 7.66 (br s, 3H), 7.10-7.04 (m, 2H), 6.85-6.80 (m, 2H), 5.45 (br s, 1H), 3.89 (t, J=7 Hz, 2H), 3.40-3.25 (m, 1H), 2.60-2.40 (m, 2H), 1.80 (dt, J=4 Hz, 13 Hz, 1H), 1.70-1.61 (m, 4H), 1.52-1.42 (m, 1H), 1.40-1.19 (m, 8H), 1.12 (s, 3H), 0.92 (t, J=7 Hz, 3H), 0.85 (t, J=7 Hz, 3H). MS (ESI+): m/z=322.2 [M+H]$^+$.

EXAMPLE 7

(1R,2R)-2-Amino-4-(4-heptyloxy-phenyl)-2-methyl-1-phenyl-butan-1-ol

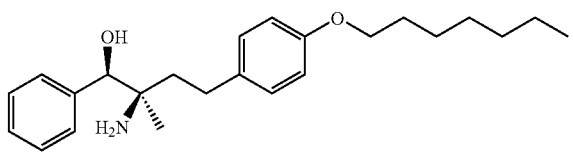

The title compound is prepared analogously to Example 1 using appropriate starting materials. The product is purified by RP-HPLC (ZORBAX Extend C-18) eluting with 5%→95% CH$_3$CN in H$_2$O (+0.1% TFA). The compound was lyophilized from dioxane to give a white, amorphous powder.

$^1$H-NMR (d6-DMSO): 7.70 (br s, 3H), 7.41-7.30 (m, 5H), 7.05-6.99 (m, 2H), 6.82-6.78 (m, 2H), 6.40 (br s, 1H), 4.66 (s, 1H), 3.88 (t, J=7 Hz, 2H), 2.67-2.41 (m, 2H), 1.70-1.59 (m, 4H), 1.40-1.20 (m, 8H), 1.11 (s, 3H), 0.85 (t, J=7 Hz, 3H). MS (ESI+): m/z=370.2 [M+H]$^+$.

EXAMPLE 8

(1S,2R)-2-Amino-4-(4-heptyloxy-phenyl)-2-methyl-1-phenyl-butan-1-ol

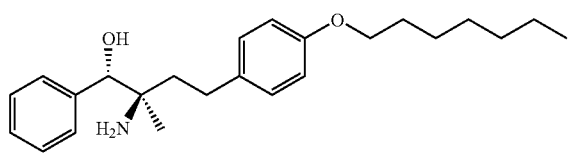

The title compound is prepared as described in Example 1 using appropriate starting materials. The compound is lyophilized from dioxane to give a white, amorphous powder.

$^1$H-NMR (d6-DMSO): 7.90 (br s, 3H), 7.40-7.28 (m, 5H), 7.00 (d, J=9 Hz, 2H), 6.79 (d, J=9 Hz, 2H), 6.40-6.36 (m, 1H), 4.70-4.65 (m, 1H), 3.88 (t, J=7 Hz, 2H), 3.33-3.28 (m, 1H), 2.60-2.40 (m, 2H), 1.89-1.78 (m, 1H), 1.69-1.61 (m, 2H), 1.45-1.20 (m, 11H), 0.85 (t, J=7 Hz, 3H). MS (ESI+): m/z=370.2 [M+H]$^+$.

EXAMPLE 9

(R)-4-Amino-6-(4-heptyloxy-phenyl)-4-methyl-hex-1-yn-3-ol

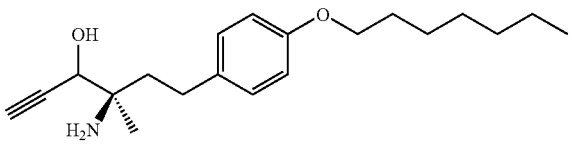

To a stirred solution of trimethylsilylacetylene (0.18 ml, 1.27 mMol) in THF (18 ml) at −78° C. is added n-Butyl-lithium (0.49 ml, 2.5 M in cyclohexane). After 5 minutes, [(R)-1-Formyl-3-(4-heptyloxy-phenyl)-1-methyl-propyl]-carbamic acid tert-butyl ester (200 mg, 0.51 mMol) in THF (2 ml) is added and the reaction is stirred at −78° C. for 5 hours. After that time, the cooling is removed and the reaction is stirred for 16 hours at RT. The reaction mixture is then poured onto a biphasic mixture of AcOEt and NaHCO$_3$ (saturated aqueous solution). The aqueous phase is extracted with AcOEt (3 times). The combined organic layers are dried (Na$_2$SO$_4$) and concentrated under reduced pressure. Column chromatography eluting with 8%-45% AcOEt in heptane gives (R)-5-Ethynyl-4-[2-(4-heptyloxy-phenyl)-ethyl]-4-methyl-oxazolidin-2-one and its C5 epimer.

To a stirred solution of (R)-5-Ethynyl-4-[2-(4-heptyloxy-phenyl)-ethyl]-4-methyl-oxazolidin-2-one in ethanol (1 ml) is added NaOH (1 ml, 1M aqueous solution). The mixture is heated at reflux temperature for 20 hours. The reaction mixture is then poured onto a biphasic mixture of AcOEt and NaHCO$_3$ (saturated aqueous solution). The aqueous phase is extracted with AcOEt (3 times). The combined organic layers are dried (Na$_2$SO$_4$) and concentrated under reduced pressure. The product is purified by RP-HPLC (ZORBAX Extend C-18) eluting with 5%→95% CH$_3$CN in H$_2$O (+0.1% TFA) to give the title compound.

$^1$H-NMR (d6-DMSO): 7.70 (br s, 3H), 7.03 (d, J=9 Hz, 2H), 6.78 (d, J=9 Hz, 2H), 4.53 (br s, 1H), 3.89 (t, J=7 Hz, 2H), 2.70-2.57 (m, 2H), 2.53 (s, 1H), 2.11-1.92 (m, 2H), 1.73 (qt, J=7 Hz, 2H), 1.50-1.21 (m, 11H), 0.85 (t, J=7 Hz, 3H). MS (ESI+): m/z=318.2 [M+H]$^+$.

EXAMPLE 10

(R)-4-Amino-6-(4-heptyloxy-phenyl)-4-methyl-hex-1-yn-3-ol (C3 epimer of example 9)

The title compound is prepared as described in Example 9 using appropriate starting materials. The product is purified by RP-HPLC (ZORBAX Extend C-18) eluting with 5%→95% CH$_3$CN in H$_2$O (+0.1% TFA) to give the title compound.

$^1$H-NMR (d6-DMSO): 7.85 (br s, 3H), 7.09 (d, J=9 Hz, 2H), 6.79 (d, J=9 Hz, 2H), 4.52 (br s, 1H), 3.90 (t, J=7 Hz, 2H), 2.75-2.50 (m, 3H), 2.23-2.12 (m, 1H), 2.10-2.00 (m,

1H), 1.75 (qt, J=7 Hz, 2H), 1.50-1.23 (m, 11H), 0.85 (t, J=7 Hz, 3H). MS (ESI+): m/z=318.2 [M+H]⁺.

EXAMPLE 11

(2S,3R)-3-Amino-5-(6-pentyloxy-naphthalen-2-yl)-3-methyl-pentan-2-ol

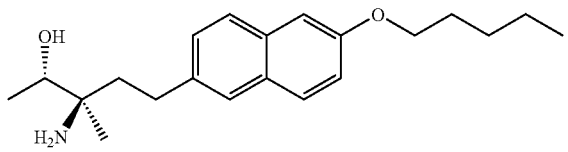

The title compound is prepared as described in Example 1 using appropriate starting materials. The compound is lyophilized from dioxane to give a white, amorphous powder.

¹H-NMR (MeOD): 7.82 (t, J=8 Hz, 2H), 7.72 (s, 1H), 7.45 (dd, J=1 Hz, 8 Hz, 1H), 7.32 (d, J=2 Hz, 1H), 7.22 (dd, J=2 Hz, 8 Hz, 1H), 4.69 (s, 3H), 4.20 (t, J=7 Hz, 2H), 3.95 (q, J=7 Hz, 1H), 2.95 (t, J=9 Hz, 2H), 2.25-2.13 (m, 1H), 2.07-1.91 (m, 3H), 1.68-1.50 (m, 7H), 1.38 (d, J=8 Hz, 3H), 1.10 (t, J=7 Hz, 3H). MS (ESI+): m/z=330.2 [M+H]⁺.

EXAMPLE 12

(2R,3R)-3-Amino-5-(6-pentyloxy-naphthalen-2-yl)-3-methyl-pentan-2-ol

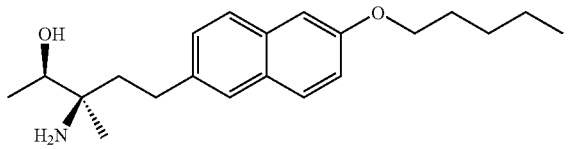

The title compound is prepared as described in Example 1 using appropriate starting materials. The compound is lyophilized from dioxane to give a white, amorphous powder.

¹H-NMR (MeOD): 7.68 (t, J=8 Hz, 2H), 7.58 (s, 1H), 7.30 (dd, J=1 Hz, 8 Hz, 1H), 7.16 (d, J=2 Hz, 1H), 7.08 (dd, J=2 Hz, 8 Hz, 1H), 4.55 (s, 3H), 4.08 (t, J=7 Hz, 2H), 3.88 (q, J=7 Hz, 1H), 2.90-2.71 (m, 2H), 2.09-1.99 (m, 1H), 1.92-1.78 (m, 3H), 1.55-1.39 (m, 4H), 1.32 (s, 3H), 1.25 (d, J=8 Hz, 3H), 0.95 (t, J=7 Hz, 3H). MS (ESI+): m/z=330.2 [M+H]⁺.

EXAMPLE 13

(2S,3R)-3-Amino-3-methyl-5-[4-(5-phenyl-pentyloxy)-phenyl]-pentan-2-ol

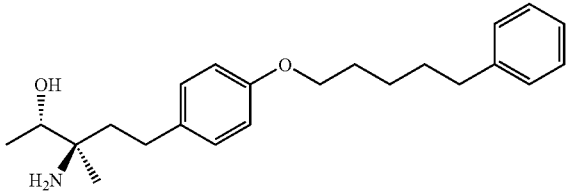

The title compound is prepared as described in Example 1 using appropriate starting materials. The compound was lyophilized from dioxane to give a white, amorphous powder.

¹H-NMR (MeOD): 7.28-7.10 (m, 7H), 6.88-6.80 (m, 2H), 4.60 (br s, 3H), 3.95 (t, J=7 Hz, 2H), 3.70 (q, J=7 Hz, 1H), 2.70-2.59 (m, 4H), 2.04-1.92 (m, 1H), 1.85-1.66 (m, 5H), 1.55-1.45 (m, 2H), 1.38 (s, 3H), 1.25 (d, J=7 Hz, 3H). MS (ESI+): m/z=356.2 [M+H]⁺.

EXAMPLE 14

(2R,3R)-3-Amino-3-methyl-5-[4-(4-phenyl-butoxy)-phenyl]-pentan-2-ol

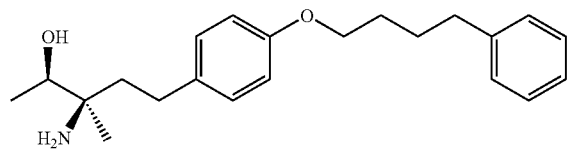

The title compound is prepared as described in Example 1 using appropriate starting materials. The compound was lyophilized from dioxane to give a white, amorphous powder.

¹H-NMR (MeOD): 7.28-7.08 (m, 7H), 6.86-6.80 (m, 2H), 4.57 (br s, 3H), 3.98-3.92 (m, 2H), 3.82 (q, J=7 Hz, 1H), 2.70-2.53 (m, 4H), 1.94-1.86 (m, 1H), 1.82-1.71 (m, 5H), 1.26 (s, 3H), 1.21 (d, J=7 Hz, 3H). MS (ESI+): m/z=342.3 [M+H]⁺.

EXAMPLE 15

(2S,3R)-3-Amino-3-methyl-5-[4-(4-phenyl-butoxy)-phenyl]-pentan-2-ol

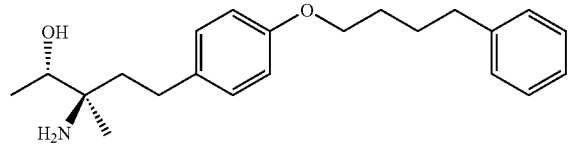

The title compound is prepared as described in Example 1 using appropriate starting materials. The compound was lyophilized from dioxane to give a white, amorphous powder.

¹H-NMR (MeOD): 7.27-7.08 (m, 7H), 6.84-6.80 (m, 2H), 4.58 (br s, 3H), 3.97-3.92 (m, 2H), 3.72 (q, J=7 Hz, 1H), 2.70-2.54 (m, 4H), 1.91-1.84 (m, 1H), 1.80-1.75 (m, 4H), 1.74-1.67 (m, 1H), 1.28 (s, 3H), 1.20 (d, J=7 Hz, 3H). MS (ESI+): m/z=342.2 [M+H]⁺.

EXAMPLE 16

(2S,3R)-3-Amino-5-[4-(2-biphenyl-4-yl-ethoxy)-phenyl]-3-methyl-pentan-2-ol

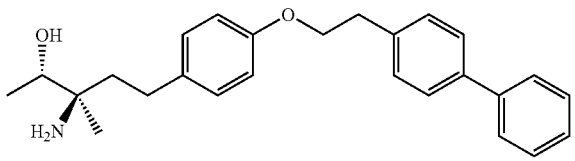

The title compound is prepared as described in Example 1 using appropriate starting materials. The compound was lyophilized from dioxane to give a white, amorphous powder.

$^1$H-NMR (MeOD): 7.64-7.55 (m, 4H), 7.47-7.38 (m, 4H), 7.36-7.30 (m, 1H), 7.17-7.12 (m, 2H), 6.90-6.85 (m, 2H), 4.60 (br s, 3H), 4.22 (t, J=7 Hz, 2H), 3.73 (q, J=7 Hz, 1H), 3.11 (t, J=7 Hz, 2H), 2.68-2.58 (m, 2H), 1.93-1.83 (m, 1H), 1.78-1.67 (m, 1H), 1.28 (s, 3H), 1.22 (d, J=7 Hz, 3H). MS (ESI+): m/z=390.2 [M+H]$^+$.

EXAMPLE 17

(2R,3R)-3-Amino-5-[4-(2-biphenyl-4-yl-ethoxy)-phenyl]-3-methyl-pentan-2-ol

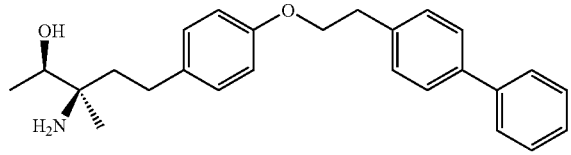

The title compound is prepared as described in Example 1 using appropriate starting materials. The compound was lyophilized from dioxane to give a white, amorphous powder.

$^1$H-NMR (MeOD): 7.67-7.58 (m, 4H), 7.50-7.40 (m, 4H), 7.39-7.33 (m, 1H), 7.17 (d, J=9 Hz, 2H), 6.90 (d, J=9 Hz, 2H), 4.60 (br s, 3H), 4.23 (t, J=7 Hz, 2H), 3.82 (q, J=7 Hz, 1H), 3.16 (t, J=7 Hz, 2H), 2.72-2.56 (m, 2H), 1.93 (dt, J=5 Hz, 14 Hz, 1H), 1.77 (dt, J=5 Hz, 14 Hz, 1H), 1.28 (s, 3H), 1.26 (d, J=7 Hz, 3H). MS (ESI+): m/z=390.3 [M+H]$^+$.

EXAMPLE 18

Phosphoric acid mono-[(1R,2R)-2-amino-4-(4-heptyloxy-phenyl)-1,2-dimethyl-butyl]ester

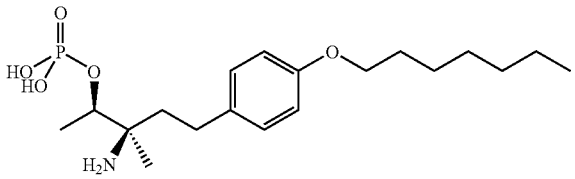

{(1R,2R)-2-(Di-tert-butoxy-phosphoryloxy)-1-[2-(4-heptyloxy-phenyl)-ethyl]-1-methyl-propyl}-carbamic acid tert-butyl ester (40 mg, 0.067 mMol) is dissolved in a saturated solution of HCl in methanol (5 ml) and stirred at RT for 24 hours. The solvent is evaporated under reduced pressure. Lyophilisation from dioxane/H$_2$O (3:1) gives the title compound as a white, amorphous powder.

$^1$H-NMR (MeOD): 7.14 (d, J=8 Hz, 2H), 6.82 (d, J=8 Hz, 2H), 4.46-4.40 (m, 1H), 3.92 (t, J=7 Hz, 2H), 2.73 (dt, J=5 Hz, 14 Hz, 1H), 2.57 (dt, J=5 Hz, 14 Hz, 1H), 2.00 (dt, J=4 Hz, 14 Hz, 1H), 1.82 (dt, J=4 Hz, 14 Hz, 1H), 1.76-1.69 (m, 2H), 1.50-1.27 (m, 14H), 0.90 (t, J=7 Hz, 3H). MS (ESI+): m/z=388.2 [M+H]$^+$, 776.4 [2M+H]$^+$.

EXAMPLE 19

Phosphoric acid mono-[(1S,2R)-2-amino-4-(4-heptyloxy-phenyl)-1,2-dimethyl-butyl]ester

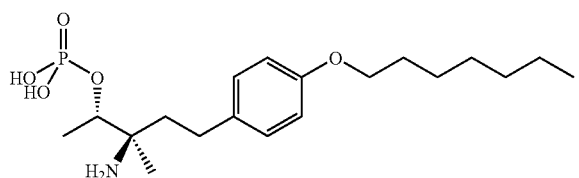

The title compound is prepared as described in Example 18 using appropriate starting materials. The compound was lyophilized from dioxane to give a white, amorphous powder.

$^1$H-NMR (MeOD): 7.13 (d, J=8 Hz, 2H), 6.83 (d, J=8 Hz, 2H), 4.38-4.31 (m, 1H), 3.93 (t, J=7 Hz, 2H), 2.70-2.58 (m, 2H), 2.02-1.94 (m, 1H), 1.88-1.79 (m, 1H), 1.78-1.70 (m, 2H), 1.48-1.27 (m, 14H), 0.90 (t, J=7 Hz, 3H). MS (ESI+): m/z=388.2 [M+H]$^+$, 776.4 [2M+H]$^+$.

EXAMPLE 20

Phosphoric acid mono-[(1R,2R)-2-amino-1,2-dimethyl-4-(6-pentyloxy-naphthalen-2-yl)-butyl]ester

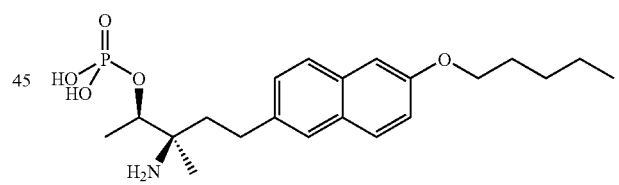

The title compound is prepared as described in Example 18 using appropriate starting materials. The compound was lyophilized from dioxane to give a white, amorphous powder.

$^1$H-NMR (d6-DMSO): 7.71-7.63 (m, 2H), 7.60 (s, 1H), 7.33 (d, J=9 Hz, 1H), 7.22 (s, 1H), 7.10-7.04 (m, 1H), 4.33-4.21 (m, 1H), 4.03 (t, J=7 Hz, 2H), 2.88-2.60 (m, 2H), 1.84-1.67 (m, 4H), 1.47-1.30 (m, 4H), 1.22 (s, 3H), 1.18 (d, J=7 Hz, 3H), 0.88 (t, J=7 Hz, 3H). MS (ESI+): m/z=432.1 [M+Na]$^+$.

The compounds of formula I in free form or in pharmaceutically acceptable salt form, exhibit valuable pharmacological properties, e.g. lymphocyte recirculation modulating properties, e.g. as indicated in in vitro and in vivo tests and are therefore indicated for therapy.

A. In Vitro

The compounds of formula I have binding affinity to individual human S1P receptors as determined in following assays:

Sphingosine-1-phosphate (S1P) Receptor Profiling

Agonist activities of compounds are tested on the human S1P receptors EDG-1 (S1P$_1$), EDG-3 (S1P$_3$), EDG-5 (S1P$_2$), EDG-6 (S1P$_4$) and EDG-8 (S1P$_5$). Functional receptor activation is assessed by quantifying compound induced GTP [γ-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-bead (Amersham-Pharmacia) immobilised SIP receptor expressing membrane protein (10-20 μg/well) in the presence of 50 mM Hepes, 100 mM NaCl, 10 mM MgCl$_2$, 10 μM GDP, 0.1% fat free BSA and 0.2 nM GTP [γ-$^{35}$S] (1200 Ci/mmol). After incubation in 96 well microtiterplates at RT for 120 min, unbound GTP [γ-$^{35}$S] is separated by a centrifugation step. Luminescence of SPA beads triggered by membrane bound GTP [γ-$^{35}$S] is quantified with a TOPcount plate reader (Packard). EC$_{50}$s are calculated using standard curve fitting software. In this assay, the compounds of formula I have a binding affinity to S1P$_1$ receptor <50 nM.

| Example | S1P$_1$ EC$_{50}$ [nM] | S1P$_3$ EC$_{50}$ [nM] | S1P$_4$ EC$_{50}$ [nM] | S1P$_5$ EC$_{50}$ [nM] |
|---|---|---|---|---|
| 18 | 0.51 Agon | 4.6 Agon | 0.70 Agon | 0.74 Agon |
| 19 | 0.07 Agon | 1.4 Agon | 0.40 Agon | 0.15 Agon |
| 20 | 0.13 Agon | 8.5 Agon | 0.67 Agon | 0.29 Agon |

Agon = agonist

B. In Vivo: Blood Lymphocyte Depletion

A compound of formula I or the vehicle is administered orally by gavage to rats. Tail blood for hematological monitoring is obtained on day −1 to give the baseline individual values, and at 2, 6, 24, 48 and 72 hours after application. In this assay, the compounds of formula I deplete peripheral blood lymphocytes when administered at a dose of 0.03 to 3 mg/kg. For example, following results are obtained: depletion of peripheral blood lymphocytes by more than 50%.

Example 1: 0.07 mg/kg p.o. after 6 h
Example 12: 0.4 mg/kg p.o. after 6 h
Example 13: 0.5 mg/kg p.o. after 6 h
Example 14: 0.1 mg/kg p.o. after 6 h
Example 15: 0.6 mg/kg p.o. after 6 h
Example 17: 0.2 mg/kg p.o. after 6 h The compounds of formula I are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves opthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, angiogenesis, Alzheimer's disease, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 0.1 to 50 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

Preferably, the compounds of formula I wherein R$_3$ is a radical of formula (d), i.e. compounds of formula I.1, are administered perorally, and preferably have the R,R configuration as shown in FIG. 1. Preferably, the compounds of formula I wherein R$_3$ is a radical of formula (e), i.e. compounds of formula I.2, are administered parenterally, and preferably have the S,R configuration as shown in FIG. 1.

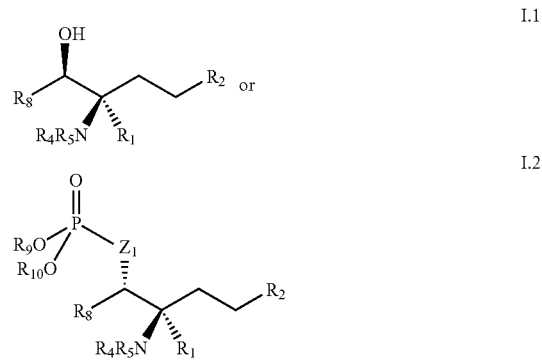

FIG. 1. Preferred Configuration of Compounds of Formula I.1 and I.2

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 or 1.2 above.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of alio- or xenograft acute or chronic rejection or inflammatory or autoimmune disorders, or a chemotherapeutic agent, e.g a malignant cell anti-proliferative agent. For example, the compounds of formula I may be used in combination with a calcineurin inhibitor, e.g. cyclosporin A, FK 506 or ISA$_{TX}$247; a mTOR inhibitor, e.g. rapamycin, 40-O-(2-hydroxyethyl)-rapamycin, CCI779, ABT578, AP23573, AP23464, AP23675, AP23841, TAFA-93, biolimus 7 or biolimus 9; an ascomycin having immunosuppressive properties, e.g. ABT-281, ASM981, etc.; corticosteroids; cyclophosphamide; azathioprene; methotrexate; leflunomide; mizoribine; mycophenolic acid or a salt thereof, e.g. sodium salt; mycophenolate mofetil; 15-deoxyspergualine or an immunosuppressive homologue, analogue or derivative thereof; immunosuppressive monoclonal antibodies, e.g. monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent.

Where the compounds of formula I are administered in conjunction with other immuno-suppressive/immunomodulatory, anti-inflammatory chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immuno-modulatory, anti-inflammatory, chemotherapeutic or anti-infectious drug, e.g. as indicated above.

6. A pharmaceutical combination, e.g. a kit, comprising a) a first agent which is a compound of formula I as disclosed herein, in free form or in pharmaceutically acceptable salt form, and b) at least one co-agent, e.g. an immunosuppressant, immunomodulatory, anti-inflammatory, chemotherapeutic or anti-infectious agent. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:

1. A compound of the formula

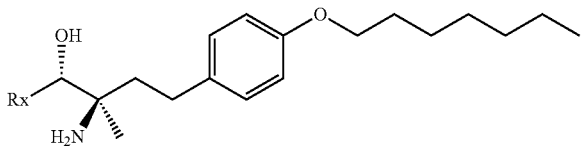

wherein $R_x$ is methyl, ethyl or phenyl,
in free form or in salt form.

2. The compound according to claim 1 having the formula

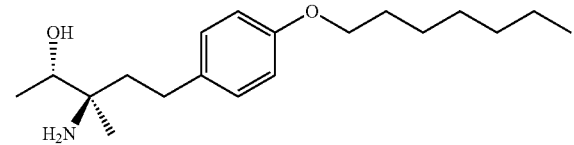

in free form or in salt form.

3. A pharmaceutical composition comprising a compound according to claim 1, in free form or in pharmaceutically-acceptable salt form, in association with a pharmaceutically-acceptable diluent or carrier therefor.

4. A pharmaceutical composition comprising a compound according to claim 1, in free form or in pharmaceutically-acceptable salt form, and one or more further agents selected from immunosuppressant agents, immunomodulatory agent, anti-inflammatory agents and anti-infectious agents.

* * * * *